United States Patent
Pianca et al.

(10) Patent No.: US 8,494,654 B2
(45) Date of Patent: Jul. 23, 2013

(54) SYSTEMS AND METHODS FOR MAKING AND USING PADDLE LEADS WITH ADJUSTABLE SPACING BETWEEN ADJACENT ELECTRODES

(75) Inventors: Anne Margaret Pianca, Santa Monica, CA (US); Priya Sundaramurthy, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 21 days.

(21) Appl. No.: 13/226,782

(22) Filed: Sep. 7, 2011

(65) Prior Publication Data
US 2012/0071936 A1 Mar. 22, 2012

Related U.S. Application Data

(60) Provisional application No. 61/385,389, filed on Sep. 22, 2010.

(51) Int. Cl.
*A61N 1/05* (2006.01)
(52) U.S. Cl.
USPC ............ 607/117; 607/116; 607/118; 607/119
(58) Field of Classification Search
USPC ................................. 607/116–119
See application file for complete search history.

(56) References Cited

U.S. PATENT DOCUMENTS

| | | | |
|---|---|---|---|
| 5,013,310 A * | 5/1991 | Goode et al. ...................... 606/1 |
| 5,417,719 A * | 5/1995 | Hull et al. ....................... 607/46 |
| 5,957,966 A * | 9/1999 | Schroeppel et al. ........... 607/122 |
| 6,161,047 A * | 12/2000 | King et al. ....................... 607/62 |
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 * | 8/2003 | Woods et al. .................... 607/46 |
| 6,741,892 B1 * | 5/2004 | Meadows et al. ............. 607/116 |
| 7,128,736 B1 | 10/2006 | Abrams et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,170,675 B2 * | 5/2012 | Alataris et al. .................. 607/46 |
| 8,244,374 B1 * | 8/2012 | Swanson ........................ 607/117 |
| 2002/0128700 A1 * | 9/2002 | Cross, Jr. ....................... 607/117 |
| 2005/0165465 A1 | 7/2005 | Pianca et al. |

(Continued)

FOREIGN PATENT DOCUMENTS
EP 0176608 9/1984

*Primary Examiner* — Joseph Stoklosa
(74) *Attorney, Agent, or Firm* — Frommer Lawrence & Haug LLP; Patrick R. Turner

(57) ABSTRACT

A paddle lead assembly for providing electrical stimulation of patient tissue includes a paddle body having a proximal end, a distal end, and a longitudinal axis. A plurality of spaced-apart electrodes are disposed on the paddle body. The plurality of spaced-apart electrodes include a first electrode and a second electrode. At least one adjustable region is configured and arranged to adjust a center-to-center distance between the first electrode and the second electrode. At least one lead body is coupled to the paddle body. A plurality of terminals are disposed on the at least one lead body. A plurality of conductive wires couple each of the electrodes to at least one of the plurality of terminals.

20 Claims, 9 Drawing Sheets

U.S. PATENT DOCUMENTS

| | | |
|---|---|---|
| 2007/0150036 A1 | 6/2007 | Anderson |
| 2007/0219595 A1 | 9/2007 | He |
| 2008/0071320 A1 | 3/2008 | Brase |
| 2012/0283808 A1* | 11/2012 | Swanson .................. 607/117 |

* cited by examiner

SYSTEMS AND METHODS FOR MAKING AND USING PADDLE LEADS WITH ADJUSTABLE SPACING BETWEEN ADJACENT ELECTRODES

CROSS-REFERENCE TO RELATED APPLICATIONS

This application claims the benefit under 35 U.S.C. §119(e) of U.S. Provisional Patent Application Ser. No. 61/385,389 filed on Sep. 22, 2010, which is incorporated herein by reference.

FIELD

The present invention is directed to the area of implantable electrical stimulation systems and methods of making and using the systems. The present invention is also directed to implantable electrical stimulation paddle leads that include adjustably-spaced electrodes, as well as methods of making and using the electrodes, paddle leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead assembly for providing electrical stimulation of patient tissue includes a paddle body having a proximal end, a distal end, and a longitudinal axis. A plurality of spaced-apart electrodes are disposed on the paddle body. The plurality of spaced-apart electrodes include a first electrode and a second electrode. At least one adjustable region is configured and arranged to adjust a center-to-center distance between the first electrode and the second electrode. At least one lead body is coupled to the paddle body. A plurality of terminals are disposed on the at least one lead body. A plurality of conductive wires couple each of the electrodes to at least one of the plurality of terminals.

In another embodiment, a paddle lead assembly for providing electrical stimulation of patient tissue includes a paddle body having a proximal end, a distal end, and a longitudinal axis. A plurality of spaced-apart electrodes are disposed on the paddle body. At least one elongated member is disposed on the paddle body. The at least one elongated member has a first end and a second end opposite to the first end. A first electrode of the plurality of electrodes is coupled to the first end of the at least one elongated member and a second electrode of the plurality of electrodes is coupled to the second end of the at least one elongated member. The at least one elongated member is formed from at least one shape memory material and is configured and arranged to bend or straighten upon activation by exposure to at least one of heat or current. The bending or straightening of the at least one elongated member causes an adjustment in center-to-center spacing between the first electrode and the second electrode along a first axis. A plurality of lead bodies are coupled to the paddle body. At least one terminal is disposed on each of the plurality of lead bodies. A plurality of conductive wires couple each of the electrodes to at least one of the plurality of terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation paddle leads that include adjustably-spaced electrodes, as well as methods of making and using the electrodes, paddle leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and U.S. Patent Applications Publication Nos. 2005/0165465; 2007/0150036; 2007/0219595; and 2008/0071320, all of which are incorporated by reference.

Figure 1:
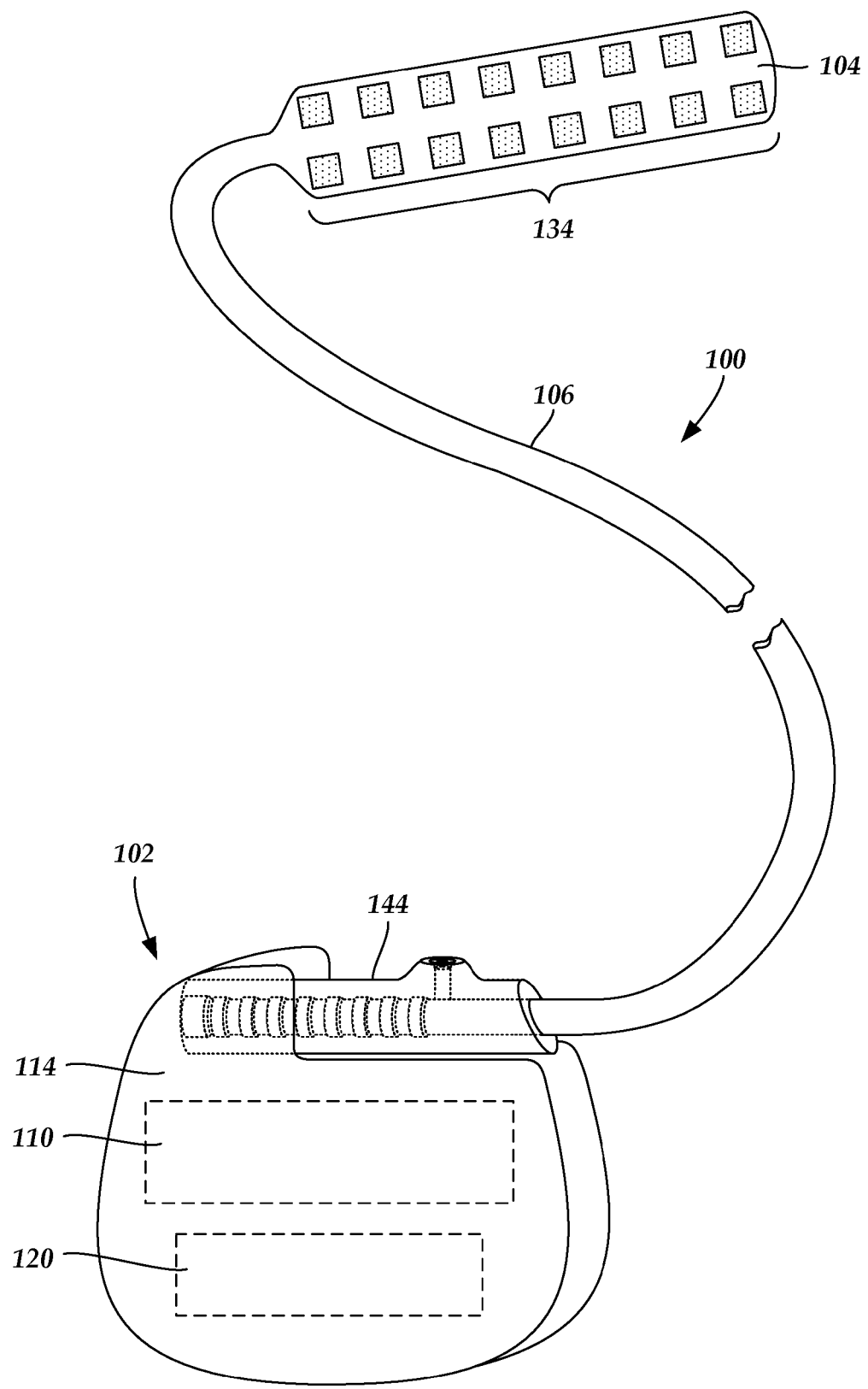
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144, 201 (FIGS. 2A and 2B, see also 222 and 250 of FIG. 2C) into which the proximal end of the one or more lead bodies 106 can be plugged to make an electrical connection via conductive contacts on the control module 102 and terminals (e.g., 210 in FIGS. 2A and 2B and 236 of FIG. 2C) on each of the one or more lead bodies 106. In addition, one or more lead extensions 212 (see FIG. 2C) can be disposed between the one or more lead bodies 106 and the control module 102 to extend the distance between the one or more lead bodies 106 and the control module 102.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 210 in FIG. 2A and 236 of FIG. 2C) are typically disposed at the proximal end of the one or more lead bodies 106 for connection to corresponding conductive contacts (e.g., 214 in FIG. 2A and 240 of FIG. 2C) in connectors (e.g., 144 in FIGS. 1-2A and 222 and 250 of FIG. 2C) disposed on, for example, the control module 102 (or to other devices, such as conductive contacts on a lead extension, an operating room cable, a splitter, or an adaptor). Conductive wires (not shown) extend from the terminals (e.g., 210 in FIG. 2A and 236 of FIG. 2C) to the electrodes 134. Typically, one or more electrodes 134 are electrically coupled to a terminal (e.g., 210 in FIG. 2A and 236 of FIG. 2C). In some embodiments, each terminal (e.g., 210 in FIG. 2A and 236 of FIG. 2C) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
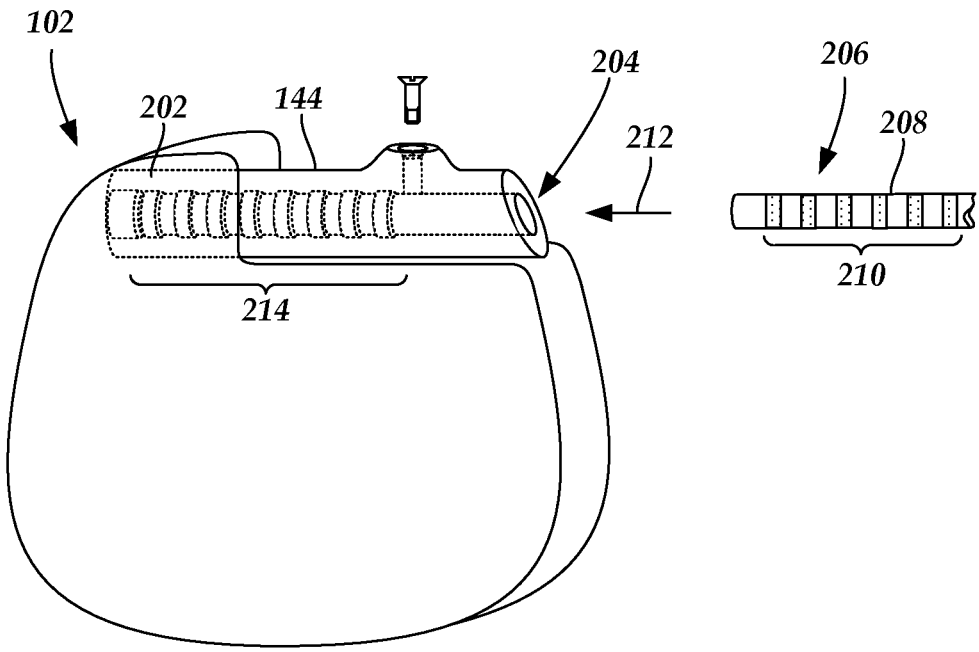
FIG. 2A is a schematic view of one embodiment of a proximal portion of a lead, a connector, and a control module of an electrical stimulation system, according to the invention.
Figure 2B:
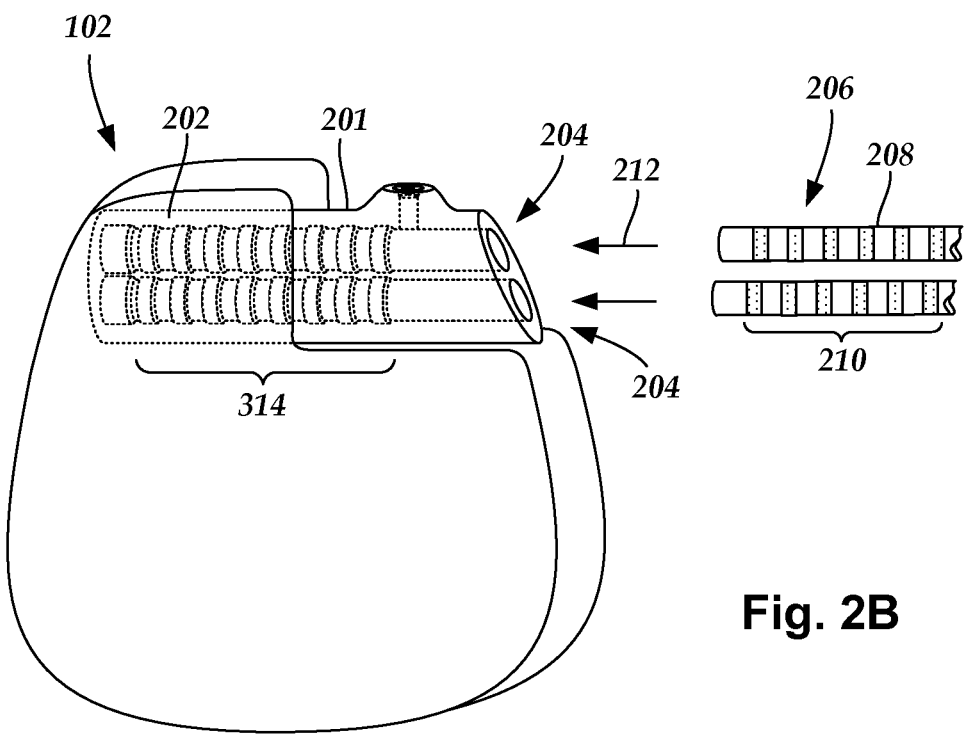
FIG. 2B is a schematic view of another embodiment of a proximal portion of a lead, a connector, and a control module of an electrical stimulation system, according to the invention.

In at least some embodiments, leads are coupled to connectors disposed on control modules. FIG. 2A is a schematic perspective view of one embodiment of the one-port connector 144 disposed on the control module 102. FIG. 2B is a schematic perspective view of one embodiment of a two-port connector 201 disposed on the control module 102. One or more leads 208 are shown configured and arranged for insertion to the control module 102. The connector 144 includes a connector housing 202. The connector housing 202 defines at least one port 204 into which a proximal end 206 of the one or more leads 208 with terminals 210 can be inserted, as shown by directional arrows 212. The connector housing 202 also includes a plurality of conductive contacts 214 within each port 204. When the one or more leads 208 are inserted into the port 204, the conductive contacts 214 can be aligned with the terminals 210 on the lead(s) 208 to electrically couple the control module 102 to the electrodes (134 of FIG. 1) disposed at a distal end of the one or more leads 208. Examples of connectors in control modules are found in, for example, U.S. Pat. No. 7,244,150 and U.S. Patent Application Publication No. 2008/0071320 A1, which are incorporated by reference.

It will be understood that the control module 102 may have any suitable number of ports including, for example, one, two, three, four, five, six, seven, eight, or more ports. It will also be understood that each of the ports can have any number of conductor contacts 214 disposed in the port. For example, in at least some embodiments, the control module has four ports, with eight conductive contacts 214 disposed in each port to define a 32-channel control module, which may be an implantable pulse generator for generating electrical pulses.

Figure 2C:
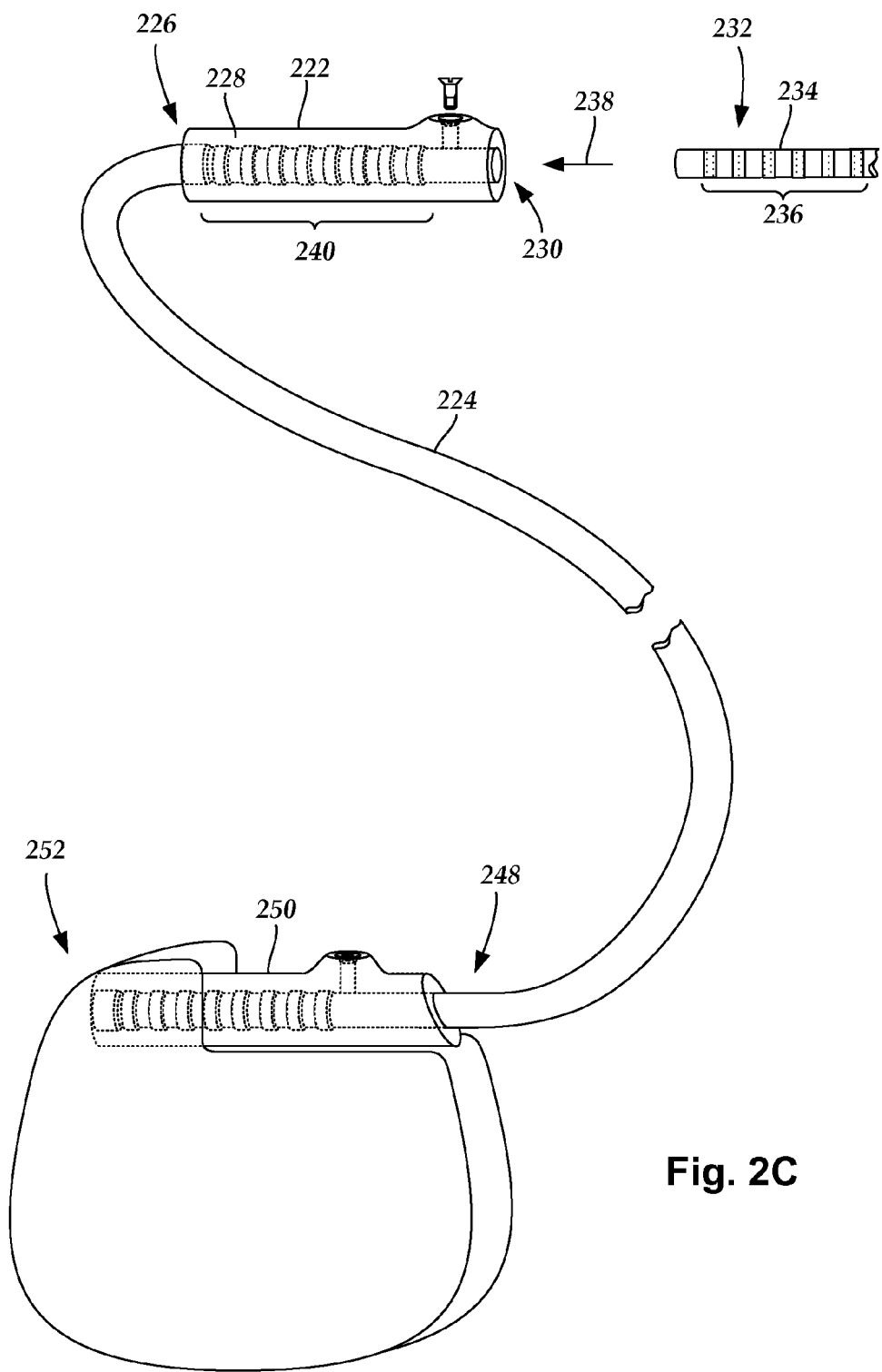
FIG. 2C is a schematic view of one embodiment of a proximal portion of a lead and a lead extension of an electrical stimulation system, according to the invention.

In FIG. 2C, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2C the proximal end 248 of the lead extension 224 is inserted into a connector 250 disposed in a control module 252.

Stimulation patterns may be affected by the relative center-to-center spacing (in any direction) between adjacent electrodes of the paddle body. Thus, the center-to-center spacing between adjacent electrodes may affect patient stimulation. For example, a particular center-to-center electrode spacing may enhance a given therapy, while a different center-to-center electrode spacing may lessen the therapy, or may cause an undesired side-effect. At least some conventional paddle leads are formed with a fixed center-to-center spacing between adjacent electrodes. Since different therapies may benefit from different center-to-center electrode spacing, it may be useful to design a paddle lead with more than a single, fixed center-to-center spacing between adjacent electrodes.

As herein described, the paddle body includes adjustable center-to-center spacing between adjacent electrodes. In at least some embodiments, the paddle body includes electrodes disposed between pleats coupled together in an accordion-like manner, where the pleats can be expanded or contracted to adjust the center-to-center spacing between adjacent electrodes. In at least some embodiments, the paddle body includes electrodes disposed on telescoping elements, where the telescoping elements can be expanded or retracted relative to one another to adjust the center-to-center spacing between adjacent electrodes. In at least some embodiments, the paddle body includes electrodes disposed on elongated members that are slidably-coupled to one another, where the elongated members can be slid relative to one another to adjust the center-to-center spacing between adjacent electrodes. In at least some embodiments, the paddle body includes electrodes coupled to plates that can be slid relative to one another, where the plates can be slid to adjust the center-to-center spacing between adjacent electrodes. In at least some embodiments, the paddle body includes electrodes coupled to elongated members formed from shape memory material that can be activated to transition between bent configurations and straight configurations, where the elongated members can be activated to adjust the center-to-center spacing between electrodes.

Figure 3:
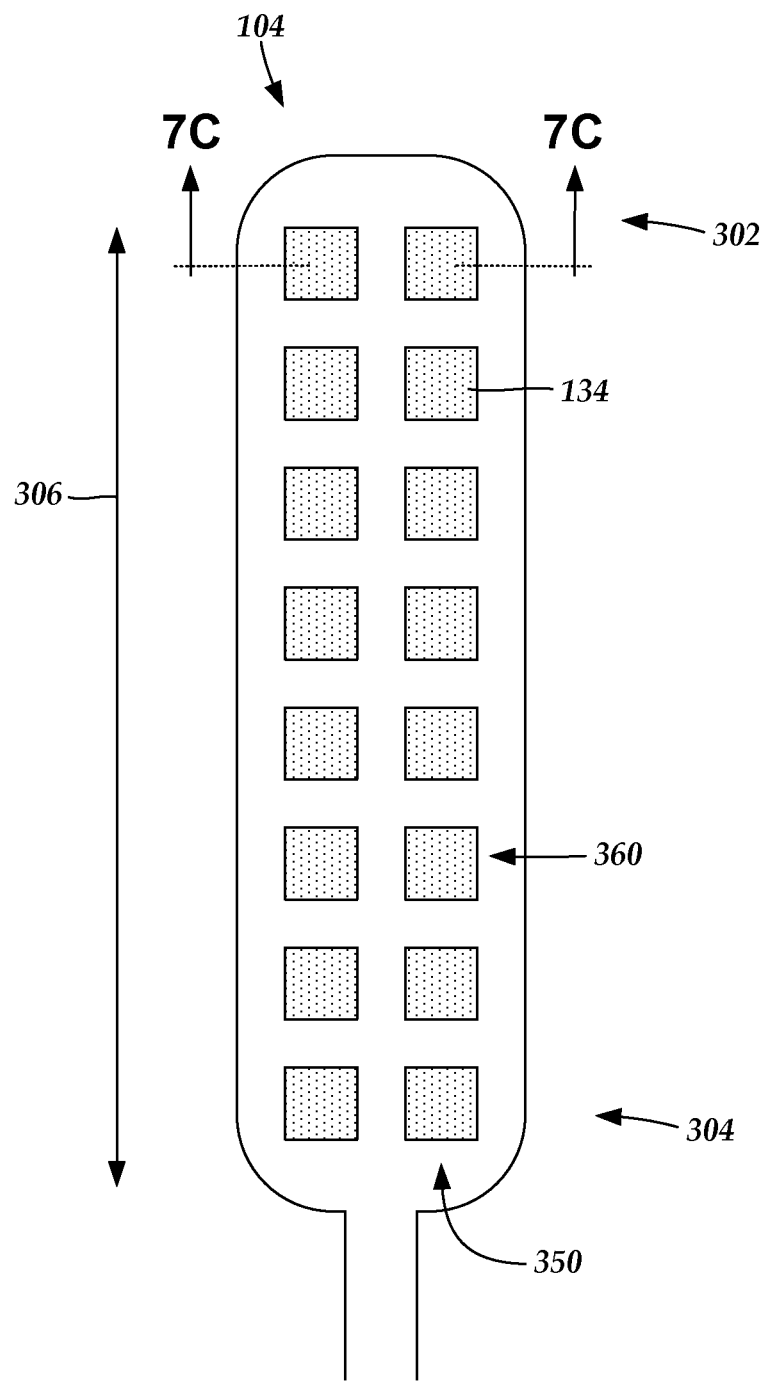
FIG. 3 is a schematic top view of one embodiment of the paddle body of FIG. 1, according to the invention.

FIG. 3 is a schematic top close-up view of one embodiment of the paddle body 104. The paddle body 104 has a distal end 302 and a proximal end 304. The paddle body 104 includes electrodes, such as electrode 134. In at least some embodiments, the electrodes 134 are arranged into columns of spaced-apart electrodes 134, such as column 350, that extend along axes parallel to a longitudinal axis 306 of the paddle body 104. In FIG. 3, the paddle body 104 is shown having two columns. It will be understood that the paddle body 104 can have any suitable number of columns including, for example, two, three, four, five, six, seven, eight, nine, ten, eleven, twelve, thirteen, fourteen, fifteen, sixteen, or more columns. In at least some embodiments, the electrodes 134 are arranged into rows of spaced-apart electrodes, such as row 360, that extend along axes perpendicular to the longitudinal axis 306 of the paddle body 104. In FIG. 3, the paddle body 104 is shown having eight rows. It will be understood that the paddle body 104 can have any suitable number of rows including, for example, one, two, three, four, five, six, seven, eight, nine, ten, eleven, twelve, thirteen, fourteen, fifteen, sixteen, or more columns.

In at least some embodiments, the paddle body 104 is configured and arranged such that center-to-center spacing between adjacent rows of electrodes 134 ("longitudinal spacing") is adjustable. In at least some embodiments, the paddle body 104 is configured and arranged such that center-to-center spacing between adjacent columns of electrodes 134 ("lateral spacing") is adjustable. In at least some embodiments, the paddle body 104 is configured and arranged such that both longitudinal and lateral spacing of electrodes are adjustable.

In at least some embodiments, the electrodes 134 can be disposed on either side of regions that can be either expanded, or contracted, or both ("expandable regions"). In at least some embodiments, the expandable regions include pleats coupled together in an accordion-like manner. Any suitable number of pleats can be coupled together to form any suitable amount of potential expansion of the expandable regions.

Figure 4A:
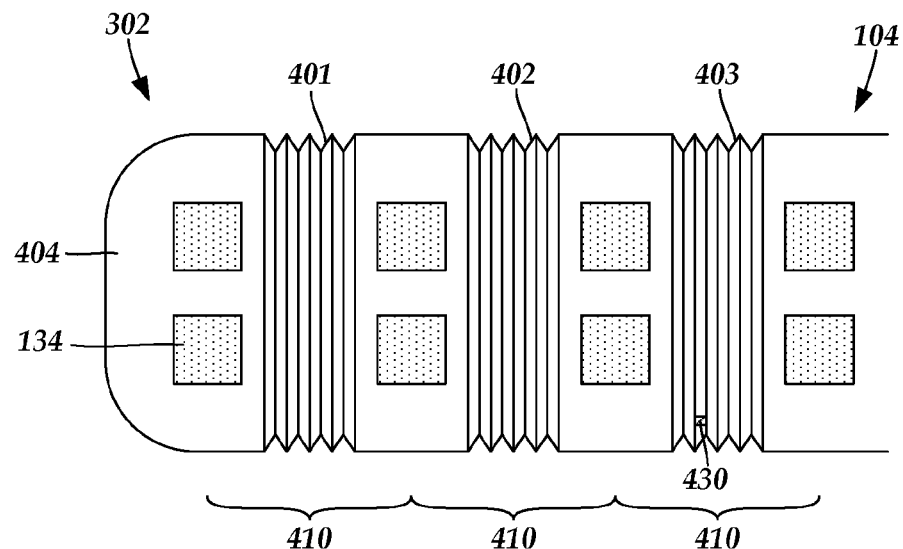
FIG. 4A is a schematic top view of one embodiment of a distal end of the paddle body of FIG. 3, the paddle body including electrodes disposed between expandable regions, the expandable regions disposed in contracted positions, according to the invention.

FIG. 4A is a schematic top view of one embodiment of the distal end 302 of the paddle body 104. The paddle body 104 includes expandable regions 401-403 disposed between electrodes 134. In FIG. 4A, the expandable regions 401-403 are shown as pleats coupled together in an accordion-like manner. The pleats can be formed from any flexible, non-conductive material suitable for implantation (e.g., silicone, polyurethane, or the like). In at least some embodiments, the pleats are configured and arranged to discourage attachment of fibrotic tissue thereon. In at least some embodiments, the pleats are smooth. In at least some embodiments, the pleats are formed such that the pleats do not extend outwardly beyond an outer surface 404 of the paddle body 104.

Any suitable number of expandable regions 401-403 can be disposed on the paddle body 104. The expandable regions 401-403 can be disposed at any suitable location on the paddle body 104. In at least some embodiments, one or more expandable regions 401-403 are disposed between adjacent rows of electrodes 134. In at least some embodiments, one or more expandable regions 401-403 are disposed between each row of the electrodes 134. It will be understood that one or more expandable regions 401-403 can alternately be used to adjust the lateral spacing of the electrodes 134 in lieu of being used to adjust the longitudinal spacing of the electrodes 134. For example, in at least some embodiments, the one or more expandable regions 401-403 are disposed between adjacent columns of the electrodes 134.

In FIG. 4A, each of the expandable regions 401-403 is disposed between two adjacent rows of the electrodes 134. The one or more expandable regions 401-403 include at least a contracted position and an expanded position. In FIG. 4A, the expandable regions 401-403 are each shown in contracted positions. When the expandable regions 401-403 are disposed between adjacent rows of the electrodes 134 and the expandable regions 401-403 are in contracted positions, the electrodes 134 of the adjacent rows have a first longitudinal center-to-center spacing 410 between the electrodes 134 of corresponding columns.

Figure 4B:
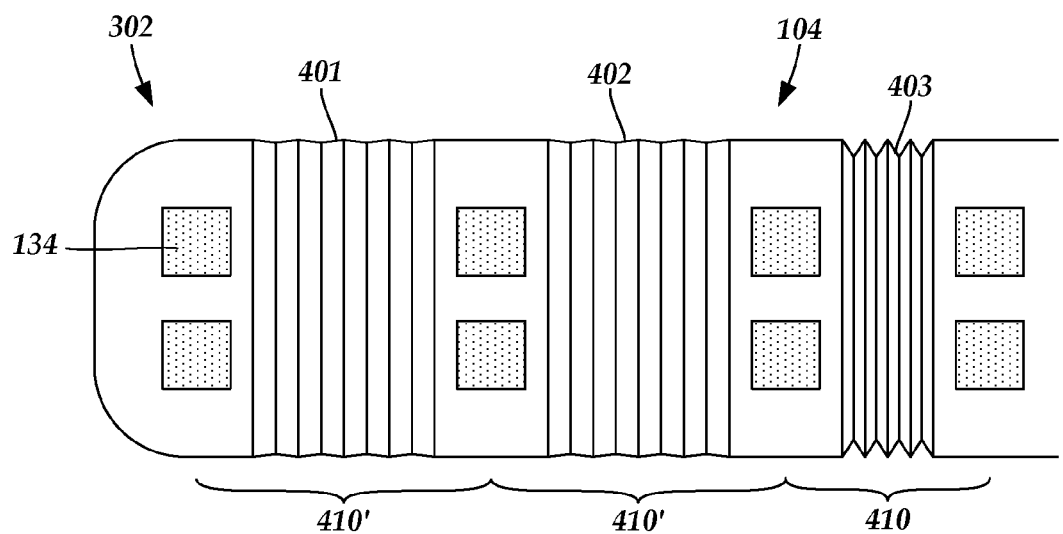
FIG. 4B is a schematic top view of one embodiment of a distal end of the paddle body of FIG. 3, the paddle body including an expandable region disposed in a contracted position and several expandable regions disposed in expanded positions, according to the invention.

FIG. 4B is a schematic top view of one embodiment of the distal end 302 of the paddle body 104. In FIG. 4B, the expandable regions 401 and 402 are shown in expanded positions, while the expandable region 403 remains in the contracted position. Consequently, the electrodes 134 of the rows flanking the expandable regions 401 and 402 each have a second longitudinal center-to-center spacing 410' between the electrodes 134 of corresponding columns that is greater than the first longitudinal center-to-center spacing 410 between the electrodes 134 of corresponding columns, as shown for the electrodes 134 of the rows flanking the expandable region 403. It will be understood that the expanded regions 401-403 can be expanded to lengths that are anywhere between the expanded positions shown by expandable regions 401 and 402 and the contracted region shown by expandable region 403. For example, one or more of the expandable regions 401-403 can be configured into partially-expanded configurations.

In at least some embodiments, the expandable regions 401-403 can be locked in at least one of the contracted position or the expanded position. In at least some embodiments, conductive wires disposed within the paddle body 104 are arranged such that the conductive wires withstand expansion and contraction of the expandable regions 401-403 without unduly stretching. For example, in at least some embodiments one or more portions of the conductive wires are disposed in the paddle body 104 in an accordion-like, coiled, or serpentine-like manner.

Expansion or contraction of the expandable regions 401-403 can be performed either manually or by an automated mechanism. In at least some embodiments, expansion or contraction of the expansion regions 401-403 can be performed using one or more fluids (e.g., air, saline solution, water, liquid glue, epoxy, or the like). In at least some embodiments, the expansion regions 401-403 include a plurality of layers of material separated from one another by a gap configured and arranged to receive the one or more fluids. In at least some embodiments, at least one of the expansion regions 401-403 includes a port 430 configured and arranged for injecting (or removing) fluid into (or from) one or more of the expansion regions 401-403 to transition one or more of the expansion regions 401-403 between the contracted position and the expanded position. In at least some embodiments, each of the expansion regions 401-403 includes the port 430 to individually control transitioning between the contracted position and the expanded position. In at least some embodiments, one port 430 can be used to collectively control transitioning between the contracted position and the expanded position for each of the expansion regions 401-403.

In at least some embodiments, the electrodes 134 can be disposed on elements that can be slid relative to one another such that the elements either extend or retract relative to each other ("telescoping elements"). In at least some embodiments, at least one of the plurality of telescoping elements is configured and arranged to retract relative to another of the telescoping elements such that the telescoping elements at least partially nest with one another. In at least some embodiments, the telescoping elements can be disposed in either a contracted (retracted) position or an expanded position.

Figure 5:
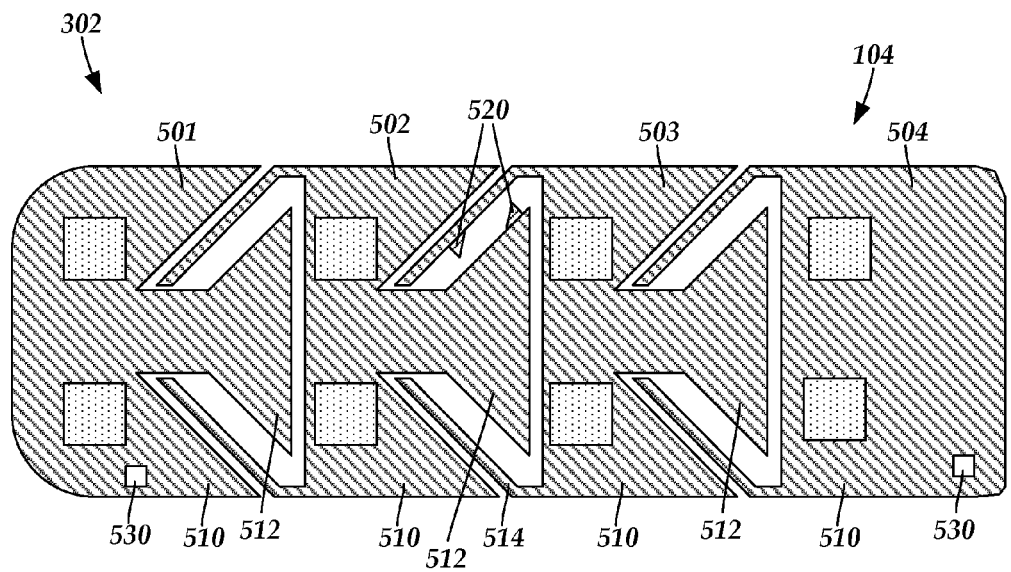
FIG. 5 is a schematic top view of one embodiment of a distal end of the paddle body of FIG. 3, the paddle body including electrodes disposed on telescoping elements that are disposed in contracted positions, according to the invention.

FIG. 5 is a schematic top view of one embodiment of the distal end 302 of the paddle body 104. The paddle body 104 includes a plurality of axially interconnected telescoping elements 501-504. At least one of the telescoping elements 501-504 is configured and arranged to at least partially nest with at least one adjacent telescoping element of the plurality of telescoping elements 501-504.

In at least some embodiments, at least one row of the electrodes 134 is disposed on each of the telescoping elements 501-504. In at least some embodiments, a single row of the electrodes 134 is disposed on each of the telescoping elements 501-504. In at least some embodiments, the telescoping elements 501-504 include a distal telescoping element 501 and a proximal telescoping element 504. In FIG. 5, the paddle body 104 includes two middle telescoping elements 502 and 503 disposed between the distal telescoping element 501 and the proximal telescoping element 504. It will be understood that the paddle body 104 may include any number of middle telescoping elements 502 and 503. Alternatively, in at least some embodiments, the paddle body 104 may not include any middle telescoping elements 502 and 503.

The telescoping elements 501-504 each include a distal portion 510 and a proximal portion 512. In at least some embodiments, the telescoping elements 501-504 are configured and arranged such that the distal portion 510 of a given telescoping element 501-504 nests with the proximal portion 512 of the immediately-distal telescoping element 501-504. In at least some embodiments, the distal portions 510 of the middle telescoping elements 502 and 503 and the proximal telescoping element 504 include a deformable distal end 514 configured and arranged to receive the proximal portion 512 of the immediately-distal telescoping element. For example, the distal end 514 of the telescoping element 503 is configured and arranged to receive the proximal portion 512 of the telescoping element 502. In at least some embodiments, the proximal portions 512 of the telescoping elements 501-503 are configured and arranged to at least partially nest within the distal portions 510 of the immediately-proximal telescoping element 502-504.

In at least some embodiments, the row of electrodes 134 disposed on the telescoping elements 501-504 are disposed on the distal portion 512 of the telescoping elements 501-504. In at least some embodiments, the proximal portions 512 of the one or more telescoping elements are shaped to mate with the bendable distal ends 514 of the distal portions 510 of proximally-adjacent telescoping elements 501-504 such that, when the telescoping elements 501-504 are slid axially apart from one another along the longitudinal axis 306 of the paddle body 104, the bendable distal ends 514 bend outwardly (laterally) in directions roughly perpendicular to the longitudinal axis 306 of the paddle body 104.

In at least some embodiments, the telescoping elements 501-504 include one or more latching mechanisms, such as latching mechanism 520, that enable the telescoping elements 501-504 to lock in place when expanded to the expanded position. In a least some embodiments, the telescoping elements 501-504 include one or more anchoring elements 530 (e.g., an aperture, a protuberance, a hook, or the like) disposed at the distal end 302 of the paddle body 104, or the proximal end of the paddle body 104, or both. In at least some embodiments, the one or more anchoring elements 530 provide one or more locations for attaching the paddle body 104 (either directly or indirectly via wire, or the like) to a patient during implantation. Attaching the paddle body 104 to the patient via the one or more anchoring elements 530 can prevent lead migration over time. Additionally, when the paddle body 104 is implanted into the patient in the expanded position, attaching the paddle body 104 to the patient via the one or more anchoring elements 530 can also maintain the paddle body 104 in the expanded position throughout the implanted lifetime of the paddle body 104 within the patient. Furthermore, when the paddle body 104 is implanted into the patient in the expanded position, attaching the paddle body 104 to the patient via the one or more anchoring elements 530 can also provide temporary anchoring (e.g., dissolving sutures, or the like).

In FIG. 5, the telescoping elements 501-504 are shown configured and arranged to adjust the longitudinal center-to-center spacing between rows of the electrodes 134. It will be understood that the telescoping elements 501-504 can, instead, be configured and arranged to adjust the lateral center-to-center spacing between columns of the electrodes 134. It will also be understood that the telescoping elements 501-504 can be extended or retracted such that the center-to-center spacing between electrodes 134 is anywhere between the extended and retracted positions.

Figure 6:
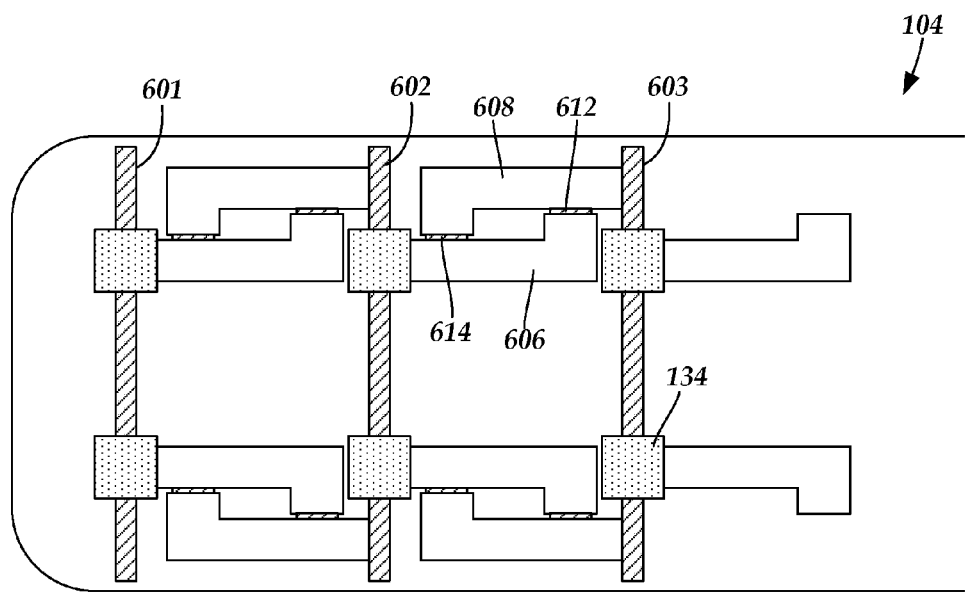
FIG. 6 is a schematic top view of one embodiment of a distal end of the paddle body of FIG. 3, the paddle body including electrodes coupled to slidably-coupleable elongated members coupled together in a contracted configurations, according to the invention.

In at least some embodiments, the electrodes 134 are coupled to corresponding elongated members that are slidably-coupled to one another. In at least some embodiments, sliding one, or both, of the elongated members relative to one another adjusts the center-to-center spacing of the electrodes 134. FIG. 6 is a schematic top view of one embodiment of the distal end 302 of the paddle body 104. The electrodes 134 are coupled to support elements 601-603. In at least some embodiments, the support elements 601-603 extend in directions that are perpendicular to the longitudinal axis 306 of the paddle body 104.

One or more elongated members are coupled to each of the support elements 601-603. For example, in FIG. 6 elongated member 606 is coupled to the support element 603 and elongated member 608 is coupled to the support element 602. At least some elongated members that are slidably-coupled to other elongated members coupled to adjacent support elements 601-603. For example, in FIG. 6 elongated member 606 is slidably-coupled to elongated member 608. In at least some embodiments, slidably-coupleable elongated members, such as slidably-coupleable elongated members 606 and 608, are coupled together via tabs, such as tabs 612 and 614 disposed on elongated members 606 and 608, respectively. In at least some embodiments, the tabs 612 and 614 are disposed at distal ends of the slidably-coupleable elongated members 606 and 608, respectively.

In at least some embodiments, sliding slidably-coupled elongated members relative to one another adjusts the spacing between the adjacent support bars 601-603 to which the slidably-coupled elongated members are coupled. Thus, sliding slidably-coupled elongated members relative to one another adjusts the longitudinal center-to-center spacing between rows of the electrodes 134 disposed on the support elements 601-603. For example, when the slidably coupleable elongated members 606 and 608 are slid relative to one another, the distance between the support elements 602 and 603 is adjusted. Accordingly, the longitudinal center-to-center spacing between rows of the electrodes 134 disposed on the support elements 602 and 603 is likewise adjusted.

In FIG. 6, the slidably coupleable elongated members are shown in a contracted position. In at least some embodiments, the slidably-coupleable elongated members are configured and arranged such that, in a contracted position the longitudinal center-to-center spacing between rows of the electrodes 134 is no more than a length of the shortest of the two slidably-coupleable elongated members that are coupled together. In at least some embodiments, the slidably-coupleable elongated members are configured and arranged such that, in an expanded position the longitudinal center-to-center spacing between rows of the electrodes 134 is no more than the combined lengths of the two slidably coupleable elongated members that are coupled together.

In FIG. 6, the slidably-coupleable elongated members are shown configured and arranged to adjust the longitudinal center-to-center spacing between rows of the electrodes 134. It will be understood that the slidably coupleable elongated members can, instead, be configured and arranged to adjust the lateral center-to-center spacing between columns of the electrodes 134, or both rows and columns. It will also be understood that the slidably-coupleable elongated members can be slid along each other such that the center-to-center spacing between electrodes 134 is anywhere between an expanded or a contracted position.

Figure 7A:
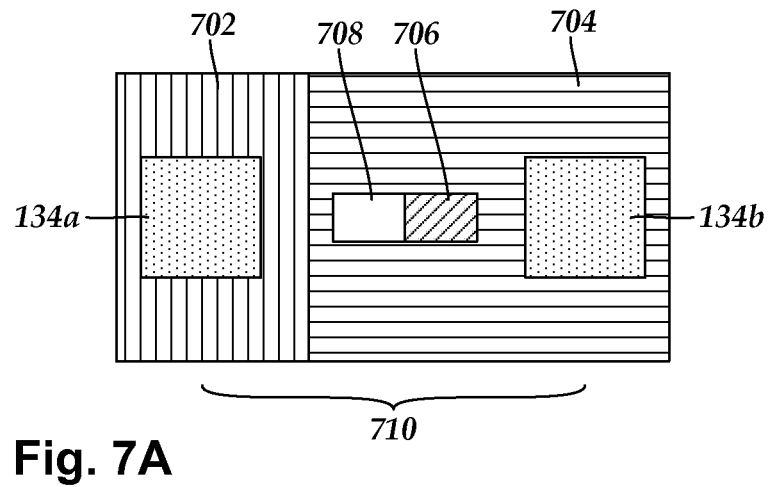
FIG. 7A is a schematic top view of one embodiment of electrodes disposed on a partially overlapping slidable plates suitable for use with the paddle body of FIG. 3, the slidable plates interconnected to one another in a contracted configuration, according to the invention.
Figure 7B:
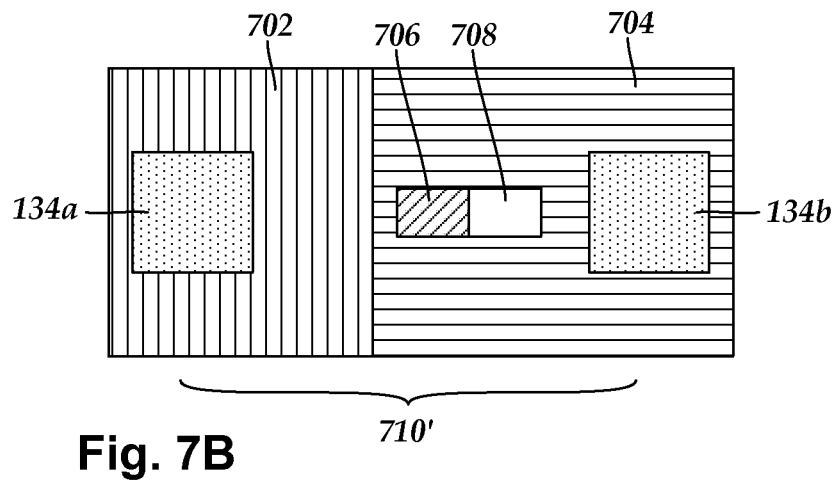
FIG. 7B is a schematic top view of one embodiment of the overlapping slidable plates of FIG. 7A, the slidable plates slid outwardly relative to one another such that the slidable plates are interconnected to one another in an expanded configuration, according to the invention.

In at least some embodiments, the paddle body includes electrodes coupled to plates that are slidably-coupled to one another such that sliding one, or both, of the plates relative to one another adjusts the center-to-center spacing of the electrodes 134. FIGS. 7A-7B are schematic top views of one embodiment of overlapping slidably-coupled plates 702 and 704 suitable for use with the paddle body 104. The electrode 134a is coupled to the plate 702 and the electrode 134b is coupled to the plate 704. The plate 702 includes a knob 706 extending from a top surface of the slidable plate 702. The plate 704 defines a slot 708 extending through the plate 704. The slot 708 defines an axis that extends between the electrodes 134a-b. The slot 708 is configured and arranged to receive the knob 706 such that, when the knob 706 is disposed in the slot 708, the knob 706 can be moved back and forth within the slot 708 along the axis of the slot 708.

In at least some embodiments, the knob 708 is fixedly coupled to the plate 702 such that movement of the knob 708 causes a corresponding movement of the plate 702.

Consequently, in at least some embodiments, movement of the knob 706 along the axis of the slot 708 causes a change in the center-to-center distance between the electrodes 134*a-b* disposed on the plates 702 and 704. In FIG. 7A, the knob 706 is positioned on one end of the slot 708 such that the electrodes 134 have a first center-to-center distance 710. In FIG. 7A, the knob 706 is positioned on an opposing end of the slot 708 such that the electrodes 134 have a second center-to-center distance 710' that is greater than the first center-to-center distance 710.

In at least some embodiments, the plates 702 and 704 can be disposed in the paddle body 104 such that the plates 702 and 704 are spaced apart laterally from one another. When the plates 702 and 704 are disposed in the paddle body 104 such that the plates 702 and 704 are spaced apart laterally from one another, moving the knob 706 along the slot 708 from the position shown in FIG. 7A to the position shown in FIG. 7B can increase the lateral center-to-center spacing between one or more columns of the electrodes 134*a-b*. In other words, moving the knob 706 along the slot 708 from the position shown in FIG. 7A to the position shown in FIG. 7B can be used to transition electrodes 134 within one or more rows from a contracted position to an expanded position.

Figure 7C:
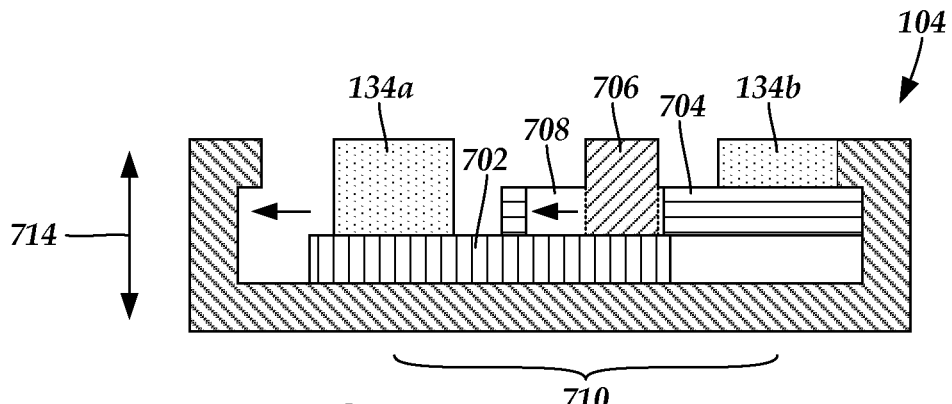
FIG. 7C is a schematic transverse cross-sectional view of one embodiment of the slidable plates of FIG. 7A disposed in a distal end of the paddle body of FIG. 3, according to the invention.

FIG. 7C is a schematic transverse cross-sectional view of one embodiment of the plates 702 and 704 disposed in the paddle body 104. In FIG. 7C, the knob 706 is shown disposed in the slot 708 such that the knob 706 is closer to the electrode 134*b* (i.e., the plates 702 and 704 are in a similar position as shown in FIG. 7A), indicating a contracted position. Thus, moving the knob 706 along the slot 708 toward the electrode 134*a* causes a transition to an expanded position.

In at least some embodiments, the electrode 134*a* has a thickness (shown in FIG. 7C as two-headed arrow 714) that is larger than the corresponding thickness of the electrode 134*b*. In at least some embodiments, the electrode 134*a* has a thickness that is equal to the combined thicknesses of both the electrode 134*b* and the plate 704.

In FIG. 7C, the slidably-coupleable plates 702 and 704 are shown configured and arranged to adjust the lateral center-to-center spacing between columns of the electrodes 134. It will be understood that the slidably-coupleable plates 702 and 704 can, instead, be configured and arranged to adjust the longitudinal center-to-center spacing between rows of the electrodes 134. It will also be understood that the slidably-coupleable plates 702 and 704 can be used in conjunction with any of the other paddle body arrangements discussed above for adjusting both the longitudinal and the lateral center-to-center spacing between adjacent electrodes. It will also be understood that the slidably-coupleable plates 702 and 704 can be slid along each other such that the center-to-center spacing between electrodes 134 is anywhere between an expanded or a contracted position.

In at least some embodiments, the paddle body 104 includes one or more elongated members formed from one or more shape memory materials, such as nitinol ("shape memory members"). In at least some embodiment, the one or more shape memory members are coupled to an activator (e.g., an electrical source, a heat source, or the like) configured and arranged to activate (e.g., bend or straighten) the shape memory members. In at least some embodiments, the shape memory members are disposed the paddle body 104 in a curved configuration. In at least some embodiments, one or more of the electrodes 134 can be coupled to the shape memory members. In at least some embodiments, one of the electrodes 134 are coupled to either end of the shape memory members. In at least some embodiments, activating the activator (e.g., applying current, applying heat, or the like) causes the shape memory members to straighten. Accordingly, when electrodes 134 are disposed at either end of one of the shape memory members, as the shape memory member straightens the spacing between the two electrodes 134 may increase. In at least some embodiments, straightened shape memory members can be de-activated to re-bend, as desired.

Figure 8A:
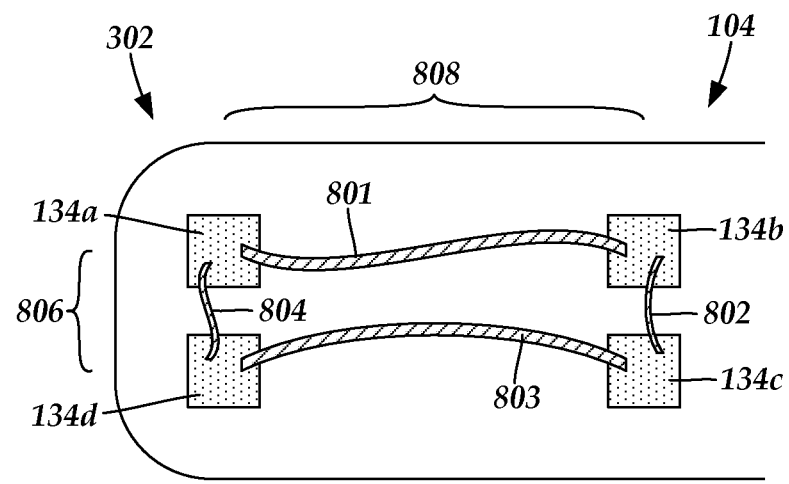
FIG. 8A is a schematic bottom view of one embodiment of a distal end of the paddle body of FIG. 3, the paddle body including electrodes coupled to elongated members formed from shape memory materials, the elongated members in bent configurations, according to the invention.

FIG. 8A is a schematic bottom view of one embodiment of the distal end 302 of the paddle body 104. The paddle body 104 includes electrodes 134*a*-134*d*. In at least some embodiments, the electrodes 134*a* and 134*d* form a first row and the electrodes 134*b* and 134*c* form a second row. The rows each have a first lateral center-to-center spacing 806 between electrodes. In at least some embodiments, the electrodes 134*a* and 134*b* form a first column and electrodes 134*c* and 134*d* form a second column. The columns each have a first longitudinal center-to-center spacing 808 between electrodes. The paddle body 104 also includes shape memory members 801-804 coupling together the electrodes 134*a-d*.

In FIG. 8A, the shape memory members 801-804 are each shown in bent configurations. The shape memory members 801-804 can be bent into any suitable shape (e.g., S-bends, arches, or the like). In FIG. 4A, the shape memory members 801 and 804 are shown with S-bends and the shape memory members 802 and 803 are shown arched. Any suitable type of bend can be used for any of the shape memory members 801-804.

In FIG. 8A, each of the electrodes 134*a-d* is shown coupled to two other of the electrodes 134*a-d*, via the shape memory members 801-804, including the electrodes 134*a-d* of the same row and column. In at least some embodiments, each of the electrodes 134*a-d* is coupled to only one other of the electrodes 134*a-d* via the shape memory members 801-804. In at least some embodiments, each of the electrodes 134*a-d* is coupled to each of the remaining electrodes 134*a-d* via the shape memory members 801-804.

In at least some embodiments, the shape memory members can be used to adjust the center-to-center spacing between electrodes of a given row (i.e., lateral spacing). In at least some embodiments, the shape memory members can be used to adjust the center-to-center spacing between electrodes of a given row without a corresponding adjustment of the center-to-center spacing between electrodes of a given column (i.e., longitudinal spacing). In at least some embodiments, each of the electrodes 134*a-d* of a given row are coupled together by one or more shape memory members 801-804 such that those electrodes 134*a-d* are not coupled to electrodes 134*a-d* disposed in any other rows. For example, in at least some embodiments, the electrodes 134*a* and 134*d* are coupled together by shape memory member 804, yet neither the electrode 134*a* nor the electrode 134*d* is coupled to either of the electrodes 134*b* and 134*c* via one or more shape memory members 801 or 803.

In at least some embodiments, the shape memory members can be used to adjust the center-to-center spacing between electrodes of a given column (i.e., longitudinal spacing). In at least some embodiments, the shape memory members can be used to adjust the center-to-center spacing between electrodes of a given column without a corresponding adjustment of the center-to-center spacing between electrodes of a given row (i.e., lateral spacing). In at least some embodiments, each of the electrodes 134*a-d* of a given column are coupled together by one or more shape memory members 801-804 such that those electrodes 134*a-d* are not coupled to electrodes 134*a-d* disposed in any other columns. For example, in at least some embodiments, the electrodes 134*a* and 134*b* are coupled together by shape memory member 8014, yet neither the electrode 134*a* nor the electrode 134*b* is coupled to either of the electrodes 134c and 134d via one or more shape memory members 802 or 804.

In FIG. 8A, the electrodes 134a-d are shown coupled together by bent shape memory members 801-804. Upon activation, one or more of the shape memory members 801-804 can be straightened, thereby increasing at least one of the lateral center-to-center spacing between two or more of the electrodes 134a-d or the longitudinal center-to-center spacing between two or more of the electrodes 134a-d. In at least some embodiments, once straightened, the one or more of the shape memory members 801-804 can be de-activated to re-bend the shape memory members 801-804, thereby decreasing at least one of the lateral center-to-center spacing between two or more of the electrodes 134a-d or the longitudinal center-to-center spacing between two or more of the electrodes 134a-d.

Figure 8B:
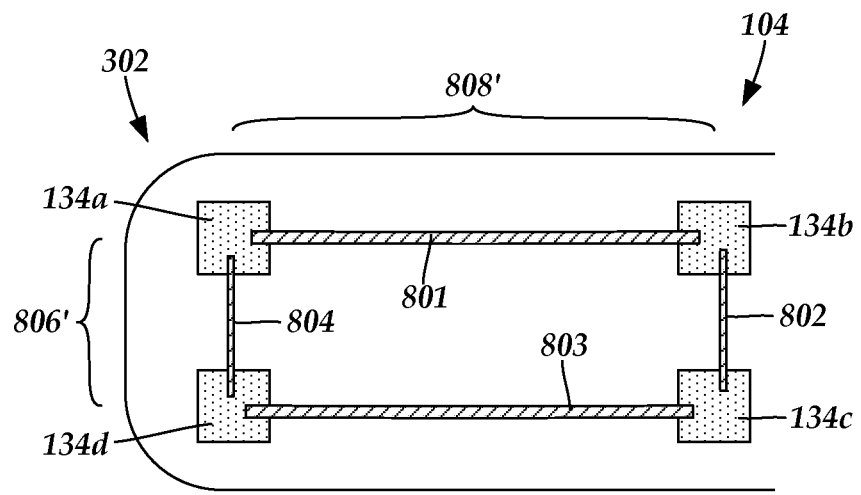
FIG. 8B is a schematic bottom view of one embodiment of a distal end of the paddle body of FIG. 3, the paddle body including electrodes coupled to the shape memory members of FIG. 8A, the shape memory members in straightened configurations, according to the invention.

FIG. 8B is a schematic bottom view of one embodiment of the distal end 302 of the paddle body 104. The shape memory members 801-804 are disposed in a straightened configuration. Accordingly, the rows of electrodes 134a-d each have a second lateral center-to-center spacing 806' between electrodes 134a-d that is greater than the first lateral center-to-center spacing 806, shown in FIG. 8A. Additionally, the columns of electrodes 134a-d each have a second longitudinal center-to-center spacing 808' between electrodes 134a-d that is greater than the first longitudinal center-to-center spacing 808 shown in FIG. 8A. It will be understood that the shape memory members 801-804 can be formed into shapes that are anywhere between the bent configurations shown in FIG. 8A and the straightened configurations shown in FIG. 8B. For example, one or more of the shape memory members 801-804 can be configured into partially-bent or partially-straightened configurations.

Figure 9:
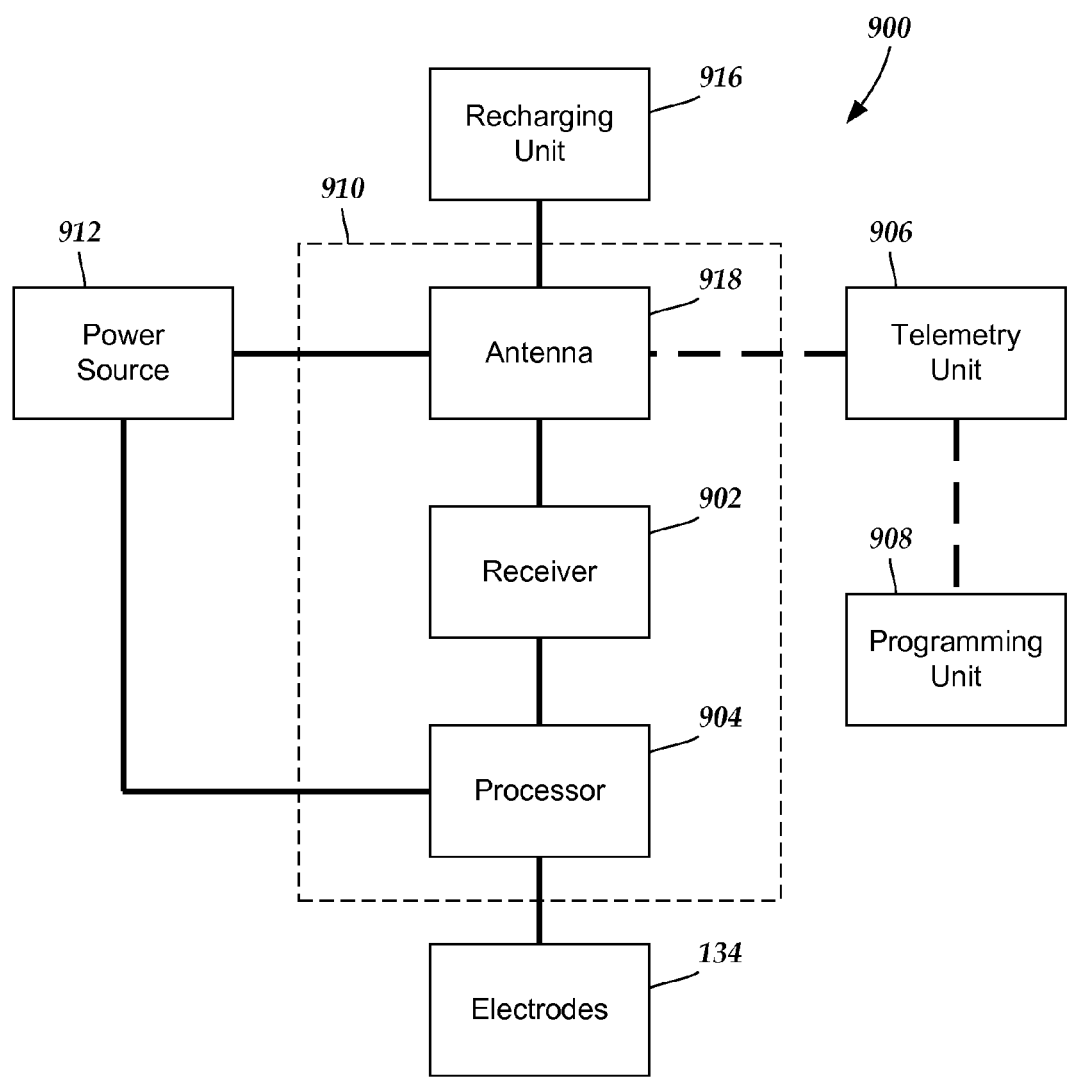
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead assembly for providing electrical stimulation of patient tissue, the paddle lead assembly comprising:
    a paddle body having a proximal end, a distal end, a longitudinal axis extending from the proximal end to the distal end of the paddle body, and a transverse axis transverse to the longitudinal axis, the paddle body comprising a major surface, the major surface having a longitudinal length along the longitudinal axis of the paddle body and a transverse width along the transverse axis of the paddle body;
    a plurality of spaced-apart electrodes disposed on, and exposed at, the major surface of the paddle body, the plurality of spaced-apart electrodes comprising a first electrode and a second electrode;
    at least one first adjustable region configured and arranged to adjust a center-to-center distance between the first electrode and the second electrode while leaving the transverse width of the major surface unchanged;
    at least one lead body coupled to the paddle body;
    a plurality of terminals disposed on the at least one lead body; and
    a plurality of conductive wires coupling each of the plurality of electrodes to at least one of the plurality of terminals.

2. The paddle lead assembly of claim 1, wherein the at least one first adjustable region comprises an expandable region disposed between the first electrode and the second electrode such that longitudinally expanding the expandable region causes a corresponding adjustment of the center-to-center distance between the first electrode and the second electrode.

3. The paddle lead assembly of claim 2, wherein the at least one first expandable region comprises a plurality of pleats coupled together in an accordion-like manner.

4. The paddle lead assembly of claim 1, wherein the at least one first adjustable region comprises a first telescoping element and an interconnected second telescoping element that is at least partially nested within the first telescoping element, wherein the second telescoping element is configured and arranged to longitudinally slide relative to the first telescoping element such that sliding the second telescoping element relative to the first telescoping element causes a corresponding adjustment of the center-to-center distance between the first electrode and the second electrode.

5. The paddle lead assembly of claim 1, wherein the at least one first adjustable region comprises a first elongated member coupled to a first support element and a second elongated member coupled to a second support element, wherein the first electrode is coupled to the first support element and the second electrode is coupled to the second support element, and wherein the first elongated member is slidably-coupled to the second elongated member such that longitudinally sliding the first elongated member relative to the second elongated member causes a corresponding adjustment of the center-to-center distance between the first electrode and the second electrode.

6. The paddle lead assembly of claim 1, wherein the at least one first adjustable region comprises a first plate and a second plate that partially overlaps the first plate, wherein the second plate defines a slot extending along the longitudinal axis of the paddle body, wherein the first plate defines a knob that extends through the slot, wherein the first electrode is disposed on the first plate and the second electrode is disposed on the second plate, and wherein the first plate and the second plate are configured and arranged such that movement of the knob along the axis of the slot causes a corresponding adjustment of the center-to-center spacing between the first electrode and the second electrode.

7. An electrical stimulating system comprising:
    the paddle lead assembly of claim 1;
    a lead extension having a proximal end and a distal end, wherein the distal end of the lead extension is configured and arranged to electrically couple to the at least one lead body of the paddle lead assembly; and
    a control module configured and arranged to electrically couple to the proximal end of the lead extension, the control module comprising
        a housing, and
        an electronic subassembly disposed in the housing.

8. The paddle lead assembly of claim 1, wherein the at least one first adjustable region is configured and arranged to adjust a longitudinal center-to-center distance between the first electrode and the second electrode along the longitudinal axis of the paddle body.

9. The paddle lead assembly of claim 8, further comprising at least one second adjustable region configured and arranged to adjust a transverse center-to-center distance between the first electrode and the second electrode along the transverse axis of the paddle body.

10. The paddle lead assembly of claim 9, wherein the at least one second adjustable region comprises a first plate and a second plate that partially overlaps the first plate, wherein the second plate defines a slot extending along the transverse axis of the paddle body, wherein the first plate defines a knob that extends through the slot, wherein the first electrode is disposed on the first plate and the second electrode is disposed on the second plate, and wherein the first plate and the second plate are configured and arranged such that movement of the knob along the axis of the slot causes a corresponding adjustment of the transverse center-to-center spacing between the first electrode and the second electrode.

11. The paddle lead assembly of claim 1, wherein the at least one first adjustable region is configured and arranged to adjust a transverse center-to-center distance between the first electrode and the second electrode along the transverse axis of the paddle body.

12. The paddle lead assembly of claim 11, further comprising at least one second adjustable region configured and arranged to adjust a longitudinal center-to-center distance between the first electrode and the second electrode along the longitudinal axis of the paddle body, the at least one second adjustable region comprising a first plate and a second plate that partially overlaps the first plate, wherein the second plate defines a slot extending along the longitudinal axis of the major surface, wherein the first plate defines a knob that extends through the slot, wherein the first electrode is disposed on the first plate and the second electrode is disposed on the second plate, and wherein the first plate and the second plate are configured and arranged such that movement of the knob along the axis of the slot causes a corresponding adjustment of the longitudinal center-to-center spacing between the first electrode and the second electrode.

13. A paddle lead assembly for providing electrical stimulation of patient tissue, the paddle lead assembly comprising:
    a paddle lead comprising
        a paddle body having a proximal end, a distal end, and a longitudinal axis extending from the proximal end to the distal end of the paddle body, and a transverse axis transverse to the longitudinal axis, the paddle body comprising a major surface, the major surface having a longitudinal length along the longitudinal axis of the paddle body and a transverse width along the transverse axis of the paddle body;

a plurality of spaced-apart electrodes disposed along the major surface of the paddle body, the plurality of spaced-apart electrodes comprising a first electrode and a second electrode at least one elongated member disposed on the major surface of the paddle body, the at least one elongated member having a first end and a second end opposite to the first end, wherein the first electrode is coupled to the first end of the at least one elongated member and the second electrode is coupled to the second end of the at least one elongated member, wherein the at least one elongated member is formed from at least one shape memory material, and wherein the at least one elongated member is configured and arranged to bend or straighten independently from the paddle lead upon activation by exposure to at least one of heat or current, the bending or straightening of the at least one elongated member causing an adjustment in center-to-center spacing between the first electrode and the second electrode along a first axis, a plurality of lead bodies coupled to the paddle body, at least one terminal disposed on each of the plurality of lead bodies, and a plurality of conductive wires coupling each of the plurality of electrodes to at least one of the plurality of terminals.

14. The paddle lead assembly of claim 13, wherein the plurality of electrodes are arranged into a plurality of rows and a plurality of columns, wherein the plurality of rows of electrodes extend perpendicular to the longitudinal axis of the paddle body and the plurality of columns of electrodes extend parallel to the longitudinal axis of the paddle body.

15. The paddle lead assembly of claim 14, wherein the first electrode and the second electrode are disposed in at least one of the same row of electrodes or the same column of electrodes.

16. The paddle lead assembly of claim 14, further comprising a third electrode, wherein the first electrode and the second electrode are disposed in different rows of electrodes, and wherein the first electrode and the third electrode are both in the same row of electrodes.

17. The paddle lead assembly of claim 16, wherein the paddle body comprises a first plate and a second plate that partially overlaps the first plate, wherein the second plate defines a slot with an axis that is perpendicular to the first axis of the paddle body and the first plate defines a knob that extends through the slot, wherein the first electrode is disposed on the first plate and the third electrode is disposed on the second plate, and wherein the first plate and the second plate are configured and arranged such that movement of the knob along the axis of the slot causes a corresponding adjustment of center-to-center spacing between he first electrode and the third electrode.

18. A paddle lead assembly for providing electrical stimulation of patient tissue, the paddle lead assembly comprising:

a paddle body having a proximal end, a distal end, a longitudinal axis extending from the proximal end to the distal end of the paddle body, and a transverse axis transverse to the longitudinal axis, the paddle body comprising a major surface, the major surface having a longitudinal length along the longitudinal axis of the paddle body and a transverse width along the transverse axis of the paddle body;

a plurality of spaced-apart electrodes disposed on, and exposed at, the major surface of the paddle body, the plurality of spaced-apart electrodes comprising a first electrode and a second electrode;

at least one adjustable region configured and arranged to adjust a center-to-center distance between the first electrode and the second electrode while leaving each of the longitudinal length and the transverse width of the major surface unchanged;

at least one lead body coupled to the paddle body;

a plurality of terminals disposed on the at least one lead body; and a plurality of conductive wires coupling each of the plurality of electrodes to at least one of the plurality of terminals.

19. The paddle lead assembly of claim 18, wherein the at least one adjustable region is configured and arranged to adjust a transverse center-to-center distance between the first electrode and the second electrode along the transverse axis of the paddle body.

20. The paddle lead assembly of claim 18, wherein the at least one adjustable region is configured and arranged to adjust a longitudinal center-to-center distance between the first electrode and the second electrode along the longitudinal axis of the paddle body.

* * * * *